United States Patent [19]
Bennett et al.

[11] Patent Number: 6,054,569
[45] Date of Patent: Apr. 25, 2000

[54] CHONDROITIN LYASE ENZYMES

[75] Inventors: D. Clark Bennett, Pierrefonds; Maryse Laliberte, Boisbriand; Kangfu Gu, Dollard des Ormeaux, all of Canada; Joseph Zimmermann, Elm Grove, Wis.; Anna Lydia Tkalec, Montreal; Dominique Fink, Chambord, both of Canada; Robert Linhardt, Iowa City, Iowa

[73] Assignee: IBEX Technologies R and D, Inc., Montreal, Canada

[21] Appl. No.: 08/931,952

[22] Filed: Sep. 17, 1997

Related U.S. Application Data

[63] Continuation of application No. 08/272,247, Jul. 8, 1994.
[51] Int. Cl.$^7$ .............................. C12N 15/60; C12N 9/88
[52] U.S. Cl. ..................... 536/23.2; 435/232; 435/320.1; 435/252.3; 424/945
[58] Field of Search ................................ 435/232, 320.1, 435/252.3; 424/94.5; 536/23.2

[56] References Cited

U.S. PATENT DOCUMENTS

| | | | |
|---|---|---|---|
| 4,390,628 | 6/1983 | Johansen | 435/189 |
| 4,696,816 | 9/1987 | Brown | 435/94 |
| 5,169,772 | 12/1992 | Zimmerman et al. | 435/232 |
| 5,292,509 | 3/1994 | Hageman | 424/94.61 |

FOREIGN PATENT DOCUMENTS

| | | |
|---|---|---|
| 54-107586 | 8/1979 | Japan . |
| 55-127988 | 10/1980 | Japan . |
| 6-98769 | 4/1994 | Japan . |

OTHER PUBLICATIONS

Baird and Klagsbrun, "The Fibroblast Growth Factor Family", Annals New York Academy of Sciences Nomenclature Meeting Report And Recommendations xi–xvi (1991).
Baker et al., "A Gene Regulating The Heat Shock Response In *Escherichia Coli* Also Affects Proteolysis", Proc. Natl. Acad. Sci., 81:6779–6783 (1984).
Cohen, et al., "Nonchromosomal Antibiotic Resistance In Bacteria; Genetic Transformation Of *Escherichia Coli* By R–Factor DNA", *Proc. Natl. Acad. Sci. USA*, 69:2110–2114 (1972).
Edman, "Phenylthiohydantoins In Protein Analysis", *Ann. N.Y. Acad. Sci.*, 88:602–610 (1950).
Folkman, et al., "A Heparin–Binding Angiogenic Protein—Basic Fibroblast Growth Factor—Is Stored Within Basement Membrand", *Am. J. Pathol.*, 130:393–400 (1988).
Folkman and Klagsbrun, "Angiongenic Factors", *Science*, 235:442–447 (1987).
Forrester, et al., "A Paradigm For Restenosis Based On Cell Biology; Clues For The Development Of New Preventive Therapies", *J. Am. Coll. Cardiol.*, 17:758–769 (1991).
Galliher, et al., "Heparinase Production By *Flavobacterium Heparinum*", *Appl. Environ. Microbiol.*, 41(2):360–365 (1981).

Gu, et al., "Comparison Of The Activity Of Two Chondroitin AC Lyases On Dermatan Sulfate", *Carbohydrate Res.*, 244:369–377 (1993).
Higashiyama, et al., "A Heparin–Binding Growth Factor Secreted By Macrophage–Like Cells That Is Related To EGF," *Science* 251:936–939 (1991).
Laemmli, "Cleavage Of Structural Proteins During The Assembly Of The Head Of Bacteriophage T4", *Nature*, 227:680–685 (1970).
Linhardt, et al., "Polysaccharide Lyases", *Appl. Biochem. Biotechnol.*, 12:135–177 (1986).
Linn, et al., "Isolation And Characterization Of Two Chondroitin Lysases From Bacteriodes Thetaiotaomicron", *J. Bacteriol.* 165:859–866 (1985).
Maniatis, et al., Molecular Cloning, A laboratory Manual (1982).
Michelacci, et al., "Isolation And Characterization Of An Induced Chondroitinase ABC From *Flavobacterium Heparinum*", *Biochimica et Biophysica Acta*, 923:291–301 (1987).
Miller, Experiments in Molecular Genetics, Cold Spring Harbor, 1972.
Nathan and Sporn, "Cytokines in Context", *J. of Cell Biol.*, 113:981–986 (1991).
Richardson and Hatton, "Transient Morphological And Biochemical Alterations Of Arterial Proteoglycan During Early Wound Healing", *Exp. Mol. Pathol.*, 58:77–95 (1993).
Sasisekharan, et al., "Heparinase Inhibits Neovascularization", *Proc. Natl. Acad. Sci. USA* 91:1524–1528 (1994).
Silhavy et al., in Experiments With Gene Fusions, Cold Spring Harbor Laboratory, 1984.
Southern, "Detection Of Specific Sequences Among DNA Fragments Separated By Gel Electrophoresis", *J. Mol. Biol.*, 98:503–517 (1975).
Tabas, et al., "Lipoprotein Lipase And Sphingomyelinase Synergistically Enhance The Association Of Atherogenic Lipoproteins With Smooth Muscle Cells And Extracellular Matrix", *J. Biol. Chem.*, 268(27):20419–20432 (1993).
Takegawa, et al., "Purification And Properties Of Chondroitinase Produced By A Bacterium Isolated From Soil", *J. Ferm. Bioeng.*, 77 (2):128–131 (1991).
Vlodavsky, et al., "Endothelial Cell–Derived Basic Fibroblast Growth Factor: Snythesis And Deposition Into Subendothelial Extracellular Matrix", *Proc. Natl. Acad. Sci. USA*, 84:2292–2296 (1987).

(List continued on next page.)

*Primary Examiner*—Rebecca E. Prouty
*Attorney, Agent, or Firm*—Arnall Golden & Gregory, LLP

[57] ABSTRACT

The present invention describes a method for the production of two highly purified enzymes capable of degrading chondroitin sulfate polysaccharides. A multi-step purification method incorporating cell disruption, cation exchange chromatography, affinity chromatography, hydroxylapatite chromatography, high resolution ion exchange chromatography and size exclusion is outlined. A 77,000±5,000 Dalton protein capable of degrading chondroitin sulfates A and C and a 55,000±2,300 Dalton protein capable of degrading dermatan sulfate were isolated. The genes encoding these enzymes, chondroitinase AC and chondroitinase B, respectively, have been cloned and methods for their use are described.

6 Claims, 4 Drawing Sheets

OTHER PUBLICATIONS

Voss et al., "Automated DNA Sequencing System Resolving 1,000 Bases With Fluorescein–15–*dATP As Interanl Label", *Meth. Molec. Cell. Biol.*, 3:153–155 (1992).

Werner, et al., "Large Induction Of Keratinocyte Growth Factor Expression In The Dermis During Wound Healing", *Proc. Natl. Acad. Sci. USA*, 89:6896–6900 (1992).

Yamagata, et al., "Purification And Properties Of Bacterial Chaondroitinases And Chondrosulfatases", *The Journal Bio. Chemistry*, 243(7):1523–1535 (1968).

Yang, et al., "Purification And Characterization Of Heparinase from Flavobacterium Heparinum", *J. Biol. Chem.*, 160(30):1849–1857 (1985).

Yeo, et al., "Alterations In Proteoglycan Synthesis Common To Healing Wounds And Tumors", *Am. J. Phatol.*, 138:1437–1450 (1991).

Dewent WPI Abstract No. 79–72510B, "Pure chondroitinase B Production", 1979.

Y. Zensaku et al., "Purification of Chomdroitinase B" Chem. Abstracts 92: 458, Abst. No. 92: 4710, Jan. 1980.

Y.M. Michelacci et al., "A Comparative Study Between a Chondroitinase B and a Chondroitinase AC From *Flavobacterium heparinum*" Biochem. J. 151: 121–129, Oct. 1975.

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 2103 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION: 1..2103
        (D) OTHER INFORMATION: /note= "Nucleic acid sequence
            encoding chondroitinase AC from Flavobacterium
            heparinum."

(xi) SEQUENCE DESCRIPTION: SEQ ID NO:1:

```
ATGAAGAAAT TATTTGTAAC CTGTATAGTC TTTTTCTCTA TTTTAAGTCC TGCTCTGCTT      60

ATTGCACAGC AGACCGGTAC TGCAGAACTG ATTATGAAGC GGGTGATGCT GGACCTTAAA     120

AAGCCTTTGC GCAATATGGA TAAGGTGGCG GAAAAGAACC TGAATACGCT GCAGCCTGAC     180

GGTAGCTGGA AGGATGTGCC TTATAAAGAT GATGCCATGA CCAATTGGTT GCCAAACAAC     240

CACCTGCTAC AATTGGAAAC TATTATACAG GCTTATATTG AAAAAGATAG TCACTATTAT     300

GGCGACGATA AAGTGTTTGA CCAGATTTCC AAAGCTTTTA AGTATTGGTA TGACAGCGAC     360

CCGAAAAGCC GCAACTGGTG GCACAATGAA ATTGCCACTC CGCAGGCCCT TGGTGAAATG     420

CTGATCCTGA TGCGTTACGG TAAAAAGCCG CTTGATGAAG CATTGGTGCA TAAATTGACC     480

GAAAGAATGA AGCGGGCGA ACCGGAGAAG AAAACGGGGG CCAACAAAAC AGATATCGCC     540
```

-continued

```
CTGCATTACT TTTATCGTGC TTTGTTAACG TCTGATGAGG CTTTGCTTTC CTTCGCCGTA     600

AAAGAATTGT TTTATCCCGT ACAGTTTGTA CACTATGAGG AAGGCCTGCA ATACGATTAT     660

TCCTACCTGC AGCACGGTCC GCAATTACAG ATATCGAGCT ACGGTGCCGT ATTTATTACC     720

GGGGTACTGA AACTTGCCAA TTACGTTAGG GATACCCCTT ATGCTTTAAG TACCGAGAAA     780

CTGGCTATAT TTTCAAAGTA TTACCGCGAC AGTTATCTGA AAGCTATCCG TGGAAGTTAT     840

ATGGATTTTA ACGTAGAAGG CCGCGGAGTA AGCCGGCCAG ACATTCTAAA TAAAAAGGCA     900

GAAAAAAGA GGTTGCTGGT GGCGAAGATG ATCGATCTTA AGCATACTGA AGAATGGGCT     960

GATGCGATAG CCAGGACAGA TAGCACAGTT GCGGCCGGCT ATAAGATTGA GCCCTATCAC    1020

CATCAGTTCT GGAATGGTGA TTATGTGCAA CATTTAAGAC CTGCCTATTC TTTTAATGTT    1080

CGTATGGTGA GTAAGCGGAC CCGACGCAGT GAATCCGGCA ATAAAGAAAA CCTGCTGGGC    1140

AGGTATTTAT CTGATGGGGC TACTAACATA CAATTGCGCG GACCAGAATA CTATAACATT    1200

ATGCCGGTAT GGGAATGGGA CAAGATTCCT GGCATAACCA GCCGTGATTA TTTAACCGAC    1260

AGACCTTTGA CGAAGCTTTG GGGAGAGCAG GGGAGCAATG ACTTTGCAGG AGGGGTGTCT    1320

GATGGTGTAT ACGGGGCCAG TGCCTACGCA TTGGATTACG ATAGCTTACA GGCAAAGAAA    1380

GCCTGGTTCT TTTTTGACAA AGAGATTGTA TGTCTTGGTG CCGGTATCAA CAGCAATGCC    1440

CCTGAAAACA TTACCACTAC CCTTAACCAG AGCTGGTTAA ATGGCCCGGT TATAAGTACT    1500

GCAGGTAAAA CCGGCCGGGG TAAAATAACA ACGTTTAAAG CACAGGGACA GTTCTGGTTG    1560

TTGCACGATG CGATTGGTTA TTACTTTCCT GAAGGGGCCA ACCTTAGTCT GAGTACCCAG    1620

TCGCAAAAAG GCAATTGGTT CCACATCAAC AATTCACATT CAAAAGATGA AGTTTCTGGT    1680

GATGTATTTA AGCTTTGGAT CAACCATGGT GCCAGGCCAG AAAATGCGCA GTATGCTTAT    1740

ATCGTTTTGC CGGGAATAAA CAAGCCGGAA GAAATTAAAA AATATAATGG AACGGCACCG    1800

AAAGTCCTTG CCAATACCAA CCAGCTGCAG GCAGTTTATC ATCAGCAGTT AGATATGGTA    1860

CAGGCTATCT TCTATACAGC TGGAAAATTA AGCGTAGCGG GCATAGAAAT TGAAACAGAT    1920

AAGCCATGTG CAGTGCTGAT CAAGCACATC AATGGCAAGC AGGTAATTTG GGCTGCCGAT    1980

CCATTGCAAA AGAAAAGAC TGCAGTGTTG AGCATCAGGG ATTTAAAAAC AGGAAAAACA    2040

AATCGGGTAA AAATTGATTT TCCGCAACAG GAATTTGCAG GTGCAACGGT TGAACTGAAA    2100

TAG                                                                2103
```

(2) INFORMATION FOR SEQ ID NO:2:

(i) SEQUENCE CHARACTERISTICS:
        (A) LENGTH: 700 amino acids
        (B) TYPE: amino acid
        (D) TOPOLOGY: linear (ii) MOLECULE TYPE: protein (ix) FEATURE:
        (A) NAME/KEY: Peptide
        (B) LOCATION: 1..23
        (D) OTHER INFORMATION: /note= "Amino acids 1 through 23
            are a leader peptide."

(ix) FEATURE:
        (A) NAME/KEY: misc_feature
        (B) LOCATION: 1..700
        (D) OTHER INFORMATION: /note= "Amino acid sequence
            of chondroitinase AC from Flavobacterium
            heparinum."

(xi) SEQUENCE DESCRIPTION: SEQ ID NO:2:

-continued

```
Met Lys Lys Leu Phe Val Thr Cys Ile Val Phe Phe Ser Ile Leu Ser
1               5                   10                  15

Pro Ala Leu Leu Ile Ala Gln Gln Thr Gly Thr Ala Glu Leu Ile Met
            20                  25                  30

Lys Arg Val Met Leu Asp Leu Lys Lys Pro Leu Arg Asn Met Asp Lys
            35                  40                  45

Val Ala Glu Lys Asn Leu Asn Thr Leu Gln Pro Asp Gly Ser Trp Lys
50                      55                  60

Asp Val Pro Tyr Lys Asp Asp Ala Met Thr Asn Trp Leu Pro Asn Asn
65                  70                  75                  80

His Leu Leu Gln Leu Glu Thr Ile Ile Gln Ala Tyr Ile Glu Lys Asp
                85                  90                  95

Ser His Tyr Tyr Gly Asp Asp Lys Val Phe Asp Gln Ile Ser Lys Ala
            100                 105                 110

Phe Lys Tyr Trp Tyr Asp Ser Asp Pro Lys Ser Arg Asn Trp Trp His
            115                 120                 125

Asn Glu Ile Ala Thr Pro Gln Ala Leu Gly Glu Met Leu Ile Leu Met
            130                 135                 140

Arg Tyr Gly Lys Lys Pro Leu Asp Glu Ala Leu Val His Lys Leu Thr
145                 150                 155                 160

Glu Arg Met Lys Arg Gly Glu Pro Glu Lys Lys Thr Gly Ala Asn Lys
                165                 170                 175

Thr Asp Ile Ala Leu His Tyr Phe Tyr Arg Ala Leu Leu Thr Ser Asp
            180                 185                 190

Glu Ala Leu Leu Ser Phe Ala Val Lys Glu Leu Phe Tyr Pro Val Gln
            195                 200                 205

Phe Val His Tyr Glu Glu Gly Leu Gln Tyr Asp Tyr Ser Tyr Leu Gln
            210                 215                 220

His Gly Pro Gln Leu Gln Ile Ser Ser Tyr Gly Ala Val Phe Ile Thr
225                 230                 235                 240

Gly Val Leu Lys Leu Ala Asn Tyr Val Arg Asp Thr Pro Tyr Ala Leu
                245                 250                 255

Ser Thr Glu Lys Leu Ala Ile Phe Ser Lys Tyr Tyr Arg Asp Ser Tyr
            260                 265                 270

Leu Lys Ala Ile Arg Gly Ser Tyr Met Asp Phe Asn Val Glu Gly Arg
            275                 280                 285

Gly Val Ser Arg Pro Asp Ile Leu Asn Lys Lys Ala Glu Lys Lys Arg
            290                 295                 300

Leu Leu Val Ala Lys Met Ile Asp Leu Lys His Thr Glu Glu Trp Ala
305                 310                 315                 320

Asp Ala Ile Ala Arg Thr Asp Ser Thr Val Ala Ala Gly Tyr Lys Ile
                325                 330                 335

Glu Pro Tyr His His Gln Phe Trp Asn Gly Asp Tyr Val Gln His Leu
            340                 345                 350

Arg Pro Ala Tyr Ser Phe Asn Val Arg Met Val Ser Lys Arg Thr Arg
            355                 360                 365

Arg Ser Glu Ser Gly Asn Lys Glu Asn Leu Leu Gly Arg Tyr Leu Ser
            370                 375                 380

Asp Gly Ala Thr Asn Ile Gln Leu Arg Gly Pro Glu Tyr Tyr Asn Ile
385                 390                 395                 400

Met Pro Val Trp Glu Trp Asp Lys Ile Pro Gly Ile Thr Ser Arg Asp
                405                 410                 415
```

Tyr Leu Thr Asp Arg Pro Leu Thr Lys Leu Trp Gly Glu Gln Gly Ser
            420                 425                 430

Asn Asp Phe Ala Gly Gly Val Ser Asp Gly Val Tyr Gly Ala Ser Ala
            435                 440                 445

Tyr Ala Leu Asp Tyr Asp Ser Leu Gln Ala Lys Lys Ala Trp Phe Phe
            450                 455                 460

Phe Asp Lys Glu Ile Val Cys Leu Gly Ala Gly Ile Asn Ser Asn Ala
465                 470                 475                 480

Pro Glu Asn Ile Thr Thr Thr Leu Asn Gln Ser Trp Leu Asn Gly Pro
                    485                 490                 495

Val Ile Ser Thr Ala Gly Lys Thr Gly Arg Gly Lys Ile Thr Thr Phe
            500                 505                 510

Lys Ala Gln Gly Gln Phe Trp Leu Leu His Asp Ala Ile Gly Tyr Tyr
            515                 520                 525

Phe Pro Glu Gly Ala Asn Leu Ser Leu Ser Thr Gln Ser Gln Lys Gly
            530                 535                 540

Asn Trp Phe His Ile Asn Asn Ser His Ser Lys Asp Glu Val Ser Gly
545                 550                 555                 560

Asp Val Phe Lys Leu Trp Ile Asn His Gly Ala Arg Pro Glu Asn Ala
                565                 570                 575

Gln Tyr Ala Tyr Ile Val Leu Pro Gly Ile Asn Lys Pro Glu Glu Ile
            580                 585                 590

Lys Lys Tyr Asn Gly Thr Ala Pro Lys Val Leu Ala Asn Thr Asn Gln
            595                 600                 605

Leu Gln Ala Val Tyr His Gln Gln Leu Asp Met Val Gln Ala Ile Phe
            610                 615                 620

Tyr Thr Ala Gly Lys Leu Ser Val Ala Gly Ile Glu Ile Glu Thr Asp
625                 630                 635                 640

Lys Pro Cys Ala Val Leu Ile Lys His Ile Asn Gly Lys Gln Val Ile
                    645                 650                 655

Trp Ala Ala Asp Pro Leu Gln Lys Glu Lys Thr Ala Val Leu Ser Ile
                    660                 665                 670

Arg Asp Leu Lys Thr Gly Lys Thr Asn Arg Val Lys Ile Asp Phe Pro
            675                 680                 685

Gln Gln Glu Phe Ala Gly Ala Thr Val Glu Leu Lys
            690                 695                 700

(2) INFORMATION FOR SEQ ID NO:3:

(i) SEQUENCE CHARACTERISTICS:
        (A) LENGTH: 1521 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION: 1..1521
        (D) OTHER INFORMATION: /note= "Nucleotide sequence
            encoding chondroitinase B from flavobacterium
            heparinum. "

(xi) SEQUENCE DESCRIPTION: SEQ ID NO:3:

ATGAAGATGC TGAATAAACT AGCCGGATAC TTATTGCCGA TCATGGTGCT GCTGAATGTG    60

-continued

```
GCACCATGCT TAGGTCAGGT TGTTGCTTCA AATGAAACTT TATACCAGGT TGTAAAGGAG    120

GTAAAACCCG GTGGTCTGGT ACAGATTGCC GATGGGACTT ATAAAGATGT TCAGCTGATT    180

GTCAGCAATT CAGGAAAATC TGGTTTGCCC ATCACTATTA AAGCCCTGAA CCCGGGTAAG    240

GTTTTTTTTA CCGGAGATGC TAAAGTAGAG CTGAGGGGCG AGCACCTGAT ACTGGAAGGC    300

ATCTGGTTTA AAGACGGGAA CAGAGCTATT CAGGCATGGA AATCACATGG ACCCGGATTG    360

GTGGCTATAT ATGGTAGCTA TAACCGCATT ACCGCATGTG TATTTGATTG TTTTGATGAA    420

GCCAATTCTG CTTACATTAC TACTTCGCTT ACCGAAGACG GAAAGGTACC TCAACATTGC    480

CGCATAGACC ATTGCAGTTT TACCGATAAG ATCACTTTTG ACCAGGTAAT TAACCTGAAC    540

AATACAGCCA GAGCTATTAA AGACGGTTCG GTGGGAGGAC CGGGGATGTA CCATCGTGTT    600

GATCACTGTT TTTTTTCCAA TCCGCAAAAA CCGGGTAATG CCGGAGGGGG AATCAGGATT    660

GGCTATTACC GTAATGATAT AGGCCGTTGT CTGGTAGACT CTAACCTGTT TATGCGTCAG    720

GATTCGGAAG CAGAGATCAT CACCAGCAAA TCGCAGGAAA ATGTTTATTA TGGTAATACT    780

TACCTGAATT GCCAGGGCAC CATGAACTTT CGTCACGGTG ATCATCAGGT GGCCATTAAC    840

AATTTTTATA TAGGCAATGA CCAGCGATTT GGATACGGGG AATGTTTGT TTGGGGAAGC     900

AGGCATGTCA TAGCCTGTAA TTATTTTGAG CTGTCCGAAA CCATAAAGTC GAGGGGGAAC    960

GCCGCATTGT ATTTAAACCC CGGTGCTATG GCTTCGGAGC ATGCTCTTGC TTTCGATATG   1020

TTGATAGCCA ACAACGCTTT CATCAATGTA AATGGGTATG CCATCCATTT TAATCCATTG   1080

GATGAGCGCA GAAAAGAATA TTGTGCAGCC AATAGGCTTA AGTTCGAAAC CCCGCACCAG   1140

CTAATGTTAA AAGGCAATCT TTTCTTTAAG GATAAACCTT ATGTTTACCC ATTTTTTAAA   1200

GATGATTATT TTATAGCAGG GAAAAATAGC TGGACTGGTA ATGTAGCCTT AGGTGTGGAA   1260

AAGGGAATCC CTGTTAACAT TTCGGCCAAT AGGTCTGCCT ATAAGCCGGT AAAAATTAAA   1320

GATATCCAGC CCATAGAAGG AATCGCTCTT GATCTCAATG CGCTGATCAG CAAAGGCATT   1380

ACAGGAAAGC CCCTTAGCTG GGATGAAGTA AGGCCCTACT GGTTAAAAGA AATGCCCGGG   1440

ACGTATGCTT TAACGGCCAG GCTTTCTGCA GATAGGGCTG CAAAGTTTAA AGCCGTAATT   1500

AAAAGAAATA AAGAGCACTG A                                             1521
```

(2) INFORMATION FOR SEQ ID NO:4:

(i) SEQUENCE CHARACTERISTICS:
        (A) LENGTH: 511 amino acids
        (B) TYPE: amino acid
        (D) TOPOLOGY: linear (ii) MOLECULE TYPE: protein (ix) FEATURE:
        (A) NAME/KEY: Peptide
        (B) LOCATION: 1..25
        (D) OTHER INFORMATION: /note= "Amino acids 1 through 25
            are a signal peptide."

(ix) FEATURE:
        (A) NAME/KEY: misc_feature
        (B) LOCATION: 1..700
        (D) OTHER INFORMATION: /note= "Amino acid sequence
            of chondroitinase B from Flavobacterium
            heparinum."

(xi) SEQUENCE DESCRIPTION: SEQ ID NO:4:

```
Met Lys Met Leu Asn Lys Leu Ala Gly Tyr Leu Leu Pro Ile Met Val
1               5                   10                  15
```

```
Leu Leu Asn Val Ala Pro Cys Leu Gly Gln Val Val Ala Ser Asn Glu
            20                  25                  30

Thr Leu Tyr Gln Val Val Lys Glu Val Lys Pro Gly Gly Leu Val Gln
            35                  40                  45

Ile Ala Asp Gly Thr Tyr Lys Asp Val Gln Leu Ile Val Ser Asn Ser
            50                  55                  60

Gly Lys Ser Gly Leu Pro Ile Thr Ile Lys Ala Leu Asn Pro Gly Lys
65                  70                  75                  80

Val Phe Phe Thr Gly Asp Ala Lys Val Glu Leu Arg Gly Glu His Leu
            85                  90                  95

Ile Leu Glu Gly Ile Trp Phe Lys Asp Gly Asn Arg Ala Ile Gln Ala
            100                 105                 110

Trp Lys Ser His Gly Pro Gly Leu Val Ala Ile Tyr Gly Ser Tyr Asn
            115                 120                 125

Arg Ile Thr Ala Cys Val Phe Asp Cys Phe Asp Glu Ala Asn Ser Ala
            130                 135                 140

Tyr Ile Thr Thr Ser Leu Thr Glu Asp Gly Lys Val Pro Gln His Cys
145                 150                 155                 160

Arg Ile Asp His Cys Ser Phe Thr Asp Lys Ile Thr Phe Asp Gln Val
            165                 170                 175

Ile Asn Leu Asn Asn Thr Ala Arg Ala Ile Lys Asp Gly Ser Val Gly
            180                 185                 190

Gly Pro Gly Met Tyr His Arg Val Asp His Cys Phe Phe Ser Asn Pro
            195                 200                 205

Gln Lys Pro Gly Asn Ala Gly Gly Ile Arg Ile Gly Tyr Tyr Arg
            210                 215                 220

Asn Asp Ile Gly Arg Cys Leu Val Asp Ser Asn Leu Phe Met Arg Gln
225                 230                 235                 240

Asp Ser Glu Ala Glu Ile Ile Thr Ser Lys Ser Gln Glu Asn Val Tyr
            245                 250                 255

Tyr Gly Asn Thr Tyr Leu Asn Cys Gln Gly Thr Met Asn Phe Arg His
            260                 265                 270

Gly Asp His Gln Val Ala Ile Asn Asn Phe Tyr Ile Gly Asn Asp Gln
            275                 280                 285

Arg Phe Gly Tyr Gly Gly Met Phe Val Trp Gly Ser Arg His Val Ile
            290                 295                 300

Ala Cys Asn Tyr Phe Glu Leu Ser Glu Thr Ile Lys Ser Arg Gly Asn
305                 310                 315                 320

Ala Ala Leu Tyr Leu Asn Pro Gly Ala Met Ala Ser Glu His Ala Leu
            325                 330                 335

Ala Phe Asp Met Leu Ile Ala Asn Asn Ala Phe Ile Asn Val Asn Gly
            340                 345                 350

Tyr Ala Ile His Phe Asn Pro Leu Asp Glu Arg Arg Lys Glu Tyr Cys
            355                 360                 365

Ala Ala Asn Arg Leu Lys Phe Glu Thr Pro His Gln Leu Met Leu Lys
            370                 375                 380

Gly Asn Leu Phe Phe Lys Asp Lys Pro Tyr Val Tyr Pro Phe Phe Lys
385                 390                 395                 400

Asp Asp Tyr Phe Ile Ala Gly Lys Asn Ser Trp Thr Gly Asn Val Ala
            405                 410                 415

Leu Gly Val Glu Lys Gly Ile Pro Val Asn Ile Ser Ala Asn Arg Ser
            420                 425                 430

Ala Tyr Lys Pro Val Lys Ile Lys Asp Ile Gln Pro Ile Glu Gly Ile
```

```
                    435                 440                 445
Ala Leu Asp Leu Asn Ala Leu Ile Ser Lys Gly Ile Thr Gly Lys Pro
    450                 455                 460

Leu Ser Trp Asp Glu Val Arg Pro Tyr Trp Leu Lys Glu Met Pro Gly
465                 470                 475                 480

Thr Tyr Ala Leu Thr Ala Arg Leu Ser Ala Asp Arg Ala Ala Lys Phe
                485                 490                 495

Lys Ala Val Ile Lys Arg Asn Lys Glu His Phe Ile Gly Arg Glu
                500                 505                 510
```

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (iv) ANTI-SENSE: NO (ix) FEATURE:
        (A) NAME/KEY: misc_feature
        (B) LOCATION: 1..29
        (D) OTHER INFORMATION: /note= "Nucleotide sequence encoding
           peptide AC-3."

(xi) SEQUENCE DESCRIPTION: SEQ ID NO:5:

TCNGGRAART ARTANCCDAT NGCRTCRTG                                       29

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (iv) ANTI-SENSE: NO (ix) FEATURE:
        (A) NAME/KEY: misc_feature
        (B) LOCATION: 1..23
        (D) OTHER INFORMATION: /note= "Nucleotide sequence encoding
           peptide AC-4."

(xi) SEQUENCE DESCRIPTION: SEQ ID NO:6:

TAYATGGAYT TYAAYGTNGA RGG                                               23

(2) INFORMATION FOR SEQ ID NO:7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (iv) ANTI-SENSE: NO (ix) FEATURE:
            (A) NAME/KEY: misc_feature
            (B) LOCATION: 3..8
            (D) OTHER INFORMATION: /note= "Nucleotides 3 through 8
                encode a BamHI site."

(xi) SEQUENCE DESCRIPTION: SEQ ID NO:7:

GCGGATCCAT GCAGCAGACC GGTACTGCAG AA                                32

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (iv) ANTI-SENSE: NO (ix) FEATURE:
        (A) NAME/KEY: misc_feature
        (B) LOCATION: 4..9
        (D) OTHER INFORMATION: /note= "Nucleotides 4 through 9
            encode a BamHI site."

(xi) SEQUENCE DESCRIPTION: SEQ ID NO:8:

CGCGGATCCC CTAGATTACT ACCATCAAAA                                  30

(2) INFORMATION FOR SEQ ID NO:9:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (iv) ANTI-SENSE: NO (ix) FEATURE:
        (A) NAME/KEY: misc_feature
        (B) LOCATION: 1..34
        (D) OTHER INFORMATION: /note= "Nucleotide sequence derived
            from the CHB-2 peptide."

(ix) FEATURE:
        (A) NAME/KEY: misc_feature
        (B) LOCATION: 3..8
        (D) OTHER INFORMATION: /note= "Nucleotides 3 through 8
            encode a BamHI site."

(xi) SEQUENCE DESCRIPTION: SEQ ID NO:9:

CGGGATCCCA RATYGCCGAY GGNACNTATA AAGA                             34

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO

```
    (iv) ANTI-SENSE: NO (ix) FEATURE:
         (A) NAME/KEY: misc_feature
         (B) LOCATION: 1..29
         (D) OTHER INFORMATION: /note= "Nucleotide sequence derived
             from the CHB-3 peptide."

(ix) FEATURE:
         (A) NAME/KEY: misc_feature
         (B) LOCATION: 3..8
         (D) OTHER INFORMATION: /note= "Nucleotides 3 through 8
             encode a BamHI site."

(xi) SEQUENCE DESCRIPTION: SEQ ID NO:10:

CGGGATCCGG CNSKATTGCG TTCRTCAAA                                     29

(2) INFORMATION FOR SEQ ID NO:11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (iv) ANTI-SENSE: NO (ix) FEATURE:
         (A) NAME/KEY: misc_feature
         (B) LOCATION: 1..34
         (D) OTHER INFORMATION: /note= "Oligonucleotide used for
             amplification of the chondroitinase B coding sequence."

(xi) SEQUENCE DESCRIPTION: SEQ ID NO:11:

CGCGGATCCA TGCAGGTGTT GCTCAAATGA AACT                               34

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (synthetic)

(iii) HYPOTHETICAL: NO (iv) ANTI-SENSE: NO (xi) SEQUENCE DESCRIPTION: SEQ ID NO:12:

CGGAATCAAT TCACCGGG                                                 18
```

CHONDROITIN LYASE ENZYMES

This is a continuation of U.S. Ser. No. 08/272,247, filed Jul. 8, 1994.

BACKGROUND OF THE INVENTION

The present invention is the purification and cloning of chondroitin lyase enzymes found in *Flavobacterium heparinum*.

Glycosaminoglycans are unbranched polysaccharides consisting of alternating hexosamine and hexuronic residues which carry sulfate groups in different positions. This class of molecules can be divided into three families according to the composition of the disaccharide backbone. These are: heparin/heparan sulfate [HexA-GlcNAc($SO_4$)]; chondroitin sulfate [HexA-GalNAc]; and keratan sulfate [Gal-GlcNAc]. The chondroitin sulfate family includes seven sub-types designated unsulfated chondroitin sulfate, oversulfated chondroitin sulfate and chondroitin sulfates A-E which vary in the number and position of their sulfate functional groups. Additionally, chondroitin sulfate B, also referred to as dermatan sulfate, differs in that iduronic acid is the predominant residue in the alternative hexuronic acid position.

Chondroitin sulfates A, B and C are the predominant forms found in mammals and may be involved in the modulation of various biological activities including cell differentiation, adhesion, enzymatic pathways and hormone interactions. The presence of chondroitin sulfate proteoglycans is elevated in the later stages of cell growth in response to tissue and vessel damage, as reported by Yeo, et al., *Am. J. Pathol.* 138:1437–1450, 1991, Richardson and Hatton, *Exp. Mol. Pathol.* 58:77–95, 1993 and Forrester, et al., *J. Am. Coll. Cardiol.* 17:758–769, 1991. Chondroitin sulfates also have been associated with events involved in the progression of vascular disease and lipoprotein uptake as described by Tabas, et al., *J. Biol. Chem.*, 268(27):20419–20432, 1993.

Chondroitin enzymes of a suitable purity and characterization could be useful tools in determining the role of chondroitin sulfates in modulating these cellular events and in developing therapeutics for the treatment of disease states.

Chondroitin sulfate degrading enzymes, referred to as chondroitinases or chondroitin sulfate lyases, from several bacterial species have been reported. Takegawa, et al., *J. Ferm. Bioeng.* 77(2):128–131, 1991, report a chondroitinase AC from Aureobacterium with a molecular weight of between 81,000 and 83,000 Daltons that is inhibited by copper ions. *Bacteriodes thetaiotamicron* produces two chondroitinase AC degrading enzymes of molecular weight 104,000 and 108,000 Daltons, as described by Linn, et al., *J. Bacteriol.* 165:859–866, 1985. Other bacterium including *Flavobacterium heparinum, Proteus vulgaris, Arthrobacter aurescens* and *Pseudomonas fluorescens* produce chondroitinase AC or chondroitinase ABC enzymes which are not well characterized, as reviewed by Linhardt, et al., *Appl. Biochem. Biotechnol.* 12:135–177, 1986. *F. heparinum* is the only microbe that produces an enzyme which is specific for dermatan sulfate, chondroitinase B, as reported by Linhardt, R., et al. However, the chondroitinase degrading enzymes from *F. heparinum* have not been purified to homogeneity or thoroughly characterized.

It is therefore an object of the present invention to provide methods for purifying chondroitin lyase enzymes.

It is a further object of the present invention to provide DNA sequences encoding chondroitin lyase enzymes.

It is a still further object of the present invention to provide purified chondroitin lyase enzymes which are useful as pharmaceutical regents.

SUMMARY OF THE INVENTION

A method for purifying chondroitin lyase enzymes from bacteria such as the Gram negative organism, *Flavobacterium heparinum*, have been developed which yields purified chondroitinase AC and chondroitinase B. Cells are grown by fermentation culture, the cells are lysed preferably using an osmotic shock technique which selectively releases proteins from the periplasmic space, then fractionated by cation exchange chromatography. Fractions containing chondroitinase degrading activity are further fractionated by affinity chromatography using a sulfated cellulose based resin and hydroxylapatite chromatography which separate the chondroitinase AC and chondroitinase B activities. Highly purified preparations of each enzyme are obtained by an additional chromatography step using a high resolution strong cation exchange resin. Pure preparations of chondroitinase B may require an additional separation step based on molecular size, such as gel filtration liquid chromatography.

The genes encoding chondroitinase AC and chondroitinase B enzymes of Flavobacterial origin were cloned. These can be used in conjunction with suitable expression systems to produce the enzymes in Flavobacterium, for example, under the control of overexpression promoters, or in organisms other than Flavobacterium.

DETAILED DESCRIPTION OF THE INVENTION

Figure 1:
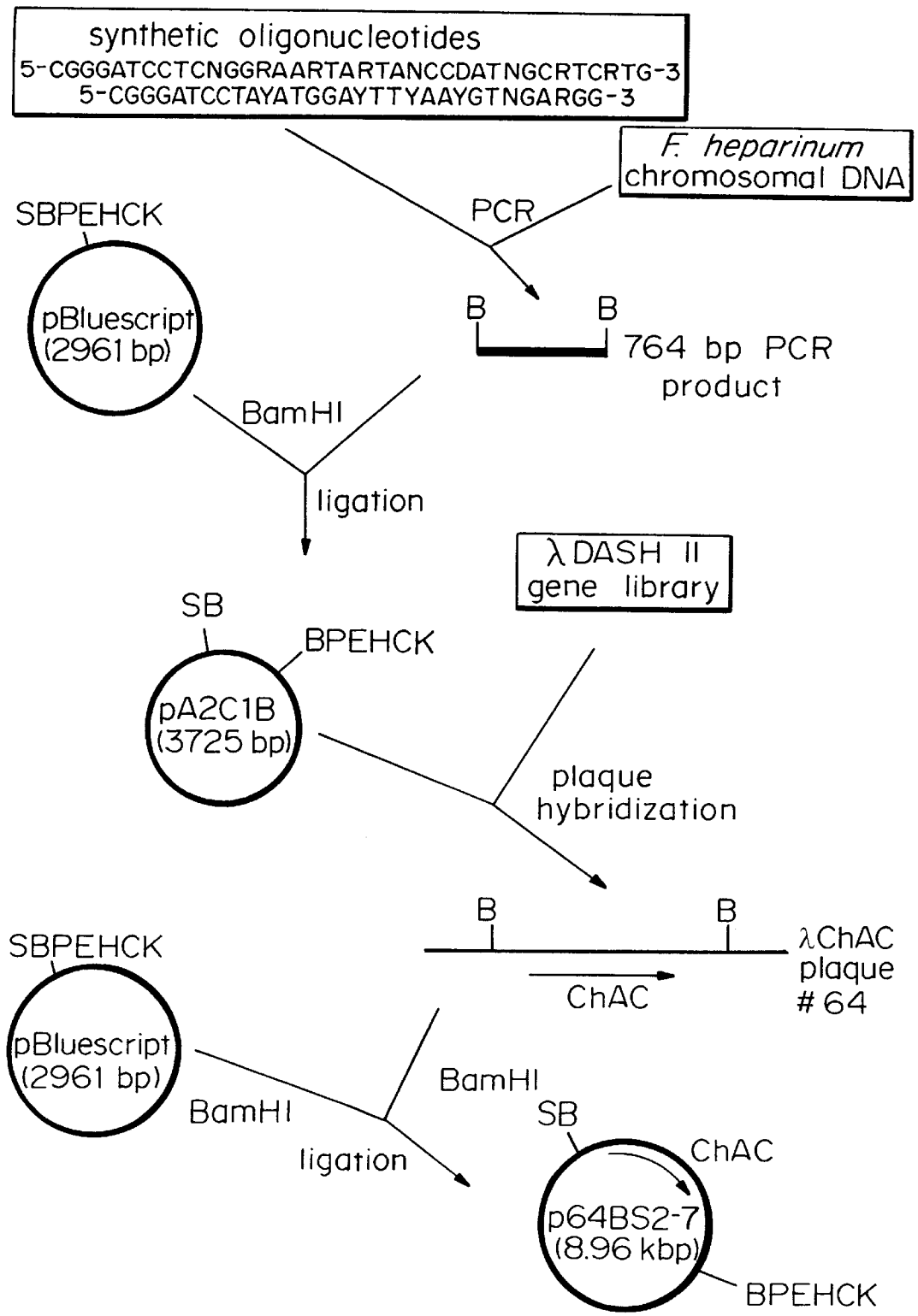
FIG. 1 is a schematic of the construction of plasmids used to sequence the chondroitinase AC gene from *Flavobacterium heparinum*, pA2C1B, p64BS2-7. Restriction sites are: S—SaU, B—BamHI, P—PstI, E—EcoRI, H—HindIII, C—ClaI and K—KpnI.

Purification of Chondroitin Sulfate degrading Enzymes from *F. heparinum*

Cells are grown in fermentation cultures to obtain sufficient quantities of the enzymes. Chondroitin sulfate A is included in the media at a concentration of between 0.5 and 10 g/l, preferably between 1.0 g/L to 2.0 g/l to induce chondroitinase AC and chondroitinase B synthesis. Crude enzyme extracts are prepared by liberating soluble proteins from the cells by standard cell disruption techniques, preferably osmotic shock based techniques which selectively release proteins from the cell's periplasmic space. For example, proteins can be released from the periplasmic space by treatment with non-ionic detergents in the range of 0.01 to 1.0%, freezing and thawing the cells, partial sonication for 0.5 to 6.0 minutes at 30 to 60% power in a pulsed mode 25/75 to 75/25, lysosyme treatment at 0.001 to 1.0 mg/ml for 15 to 60 minutes between 4 and 25° C., organic solvent treatment with 0.01 to 1.0% chloroform or toluene or by the osmotic shock process described in U.S. Pat. No.

5,169,772 to Zimmermann and Cooney. In the latter, cells are partially sonicated for between 0.5 and 4.0 minutes, poser 3–6 pulsed mode 50/50, partial homogenization 250 to 500 psi, followed by lysozyme treatment at 0.001 to 1.0 mg/ml for between 15 and 60 minutes at between 4 and 23° C., and organic solvent treatment with 0.01 to 1.0% chloroform or 0.01 to 1.0% toluene.

In the preferred embodiment, the crude extract is fractionated by cation exchange chromatography using a high flow rate resin such as Sepharose™ S Big Beads (Pharmacia), MonoS™ (Pharmacia), CBX (J. T. Baker), Sepharose™ S(Pharmacia), and CM cellulose (Bio-Rad or Sigma), at a pH of between 6.0 and 8.5 with a salt gradient equivalent to 0.01 to 1.0 M NaCl. The bound proteins are preferably eluted with step gradients of 0.25 M sodium chloride and 1.0 M sodium chloride, at pH 7.0. Chondroitinase activity elutes in the 0.25 M sodium chloride fraction. Other salts can be utilized, such as sodium phosphate or sodium sulfate to create the salt gradient. Alternatively, a pH gradient in the range of 6.0 to 10.0 could be employed or a combination of a salt and pH gradient.

Fractions containing chondroitinase degrading activity are further fractionated by affinity chromatography using a sulfated cellulose based resin with a linear gradient of 0.0 to 0.4 M NaCl. Chondroitinase AC primarily elutes at 0.23 to 0.26 M NaCl and chondroitinase B elutes at 0.27 to 0.3 M NaCl. This is followed by hydroxylapatite chromatography using a step gradient of 0.25 M NaCl followed by a linear gradient of 0.25 to 1.0 M NaCl at pH 7.7. Chondroitinase B elutes at 0.25 M NaCl while chondroitinase AC elutes at 0.85 to 0.95 M NaCl. Highly purified preparations of each enzyme are obtained using a high resolution strong cation exchange resin eluted with a linear gradient from 0.125 to 0.325 M NaCl in 0.025 M sodium phosphate at pH 7.0±0.1, as described with reference to elution from cation exchange resins described above. Chondroitinase B elutes in a protein peak at 0.175 to 0.225 M NaCl. Chondroitinase B can be further purified on the basis of molecular size by size exclusion chromatography, ultrafiltration or preparative gel electrophoresis. Gel filtration (size exclusion) resins with maximum resolution performance in the range of 5,000 to 100,000 are preferred. These include Superose™ 12, Superose™ 6, Sephadex™ G-50 and Sephadex™ G-50 from Pharmacia and BioGel™ P-60 and BioGel™ P-100 from BioRad. Ultrafiltration or dialysis membranes with molecular weight cutoffs in the range of 10,000 to 30,000 Daltons are useful in removing small contaminants while ultrafiltration and dialysis membranes with molecular weight cut-offs in the range of 70,000 to 1,000,000 Daltons are useful to remove larger contaminants. Alternatively, chondroitinase B containing samples of sufficient purity, more than 25% pure, could be further purified by subjecting the sample to gel electrophoresis according to standard laboratory procedures, and excising the major band appearing at a molecular weight of 55,000±2,300 Daltons.

The method of producing and purifying the chondroitinase lyase enzymes is exemplified as follows.

*F. heparinum* was cultured in 15 L computer controlled fermenters in a variation of the defined nutrient medium described by Galliher, et al., *Appl. Environ. Microbiol.* 41(2):360–365, 1981. Chondroitin sulfate A (Sigma) was included in the media at a concentration of 1.0 g/L as the inducer of chondroitinase AC and chondroitinase B synthesis. The cells were harvested by centrifugation and the desired enzymes released from the periplasmic space by a variation of the osmotic shock procedure described by U.S. Pat. No. 5,169,772 to Zimmermann and Cooney. Cells were resuspended in 0.01 M sodium phosphate and 0.3 M sodium chloride at pH 7.0±0.1 to give a final cell concentration of 100 absorbance units at 600 nm. The non-ionic detergent Nonedit™ P-40 was added to the cell suspension to a final concentration of 0.1% and the cells stirred for 1 hour at room temperature using a magnetic stir bar device. Cells and cell debris were then removed by centrifugation using a Sorval™ RC5C centrifuge with a JA-10 rotor at 10,000 RPM for 45 minutes. The cell pellet was discarded and the osmolate supernatant retained for further processing.

Osmolates obtained from *F. heparinum* fermentations induced with chondroitin sulfate A were subjected to centrifugation to remove cells and cell debris and the supernatant applied to a cation exchange column (5.0 cm×30 cm, Sepharose™ S Big Beads, Pharmacia) at a linear flow rate of 10 cm.min$^{-1}$. The bound proteins were eluted at a linear flow rate of 5.1 cm.min$^{-1}$ with step gradients of 0.01 M phosphate, 0.01 M phosphate/0.25 M sodium chloride and 0.01 M phosphate/1.0 M sodium chloride, all at pH 7.0±0.1. Chondroitinase activity eluted in the 0.25 M sodium chloride fraction.

This fraction was further purified by diluting the chondroitinase containing fraction two-fold with 0.01 M sodium phosphate and applying the material onto a column containing cellufine sulfate (2.6 cm i.d.×100 cm, Amicon) and eluting at a linear flow rate of 1.88 cm.min$^{-1}$ with a linear gradient of sodium chloride, 0.0 to 0.4 M. Chondroitinase AC primarily eluted at 0.23 to 0.26 M sodium chloride while chondroitinase B eluted at 0.27 to 0.3 M sodium chloride.

Each fraction was diluted two-fold with 0.01 M sodium phosphate and applied to a hydroxylapatite column (2.6 cm i.d.×30 cm). The bound proteins were eluted with a step gradient of 0.25 M sodium chloride followed by a linear gradient of 0.25 to 1.0 M sodium chloride all in 0.025 M sodium phosphate at pH 7.7±0.1. Chondroitinase B elutes in the 0.25 M sodium chloride step while chondroitinase AC elutes at 0.85 to 0.95 M sodium chloride.

The chondroitinase B fraction was diluted two-fold in 0.01 M sodium phosphate and applied to a strong cation exchange column (CBX-S, J. T. Baker, 1.6 cm i.d.×10 cm). The bound material was eluted at a flow rate of 1.0 cm.min$^{-1}$ with a linear gradient from 0.125 to 0.325 M sodium chloride in 0.025 M sodium phosphate at pH 7.0±0.1. Chondroitinase B eluted in a protein peak at 0.175 to 0.225 M sodium chloride and contained a minor contaminating protein of molecular weight 20,000 Daltons. This protein was removed by gel filtration chromatography by loading the chondroitinase B sample onto a Superdex™ 200 column (1.0 cm i.d.×30 cm, Pharmacia) and eluting with 0.05 M sodium phosphate, pH 7.2 at a linear flow rate of 1.25 cm.min$^{-1}$ and collecting the protein containing fractions.

The chondroitinase AC fraction collected from hydroxylapatite chromatography was diluted three-fold in 0.01 M sodium phosphate and applied to a strong cation exchange column (CBX-S, J. T. Baker, 1.6 cm i.d.×10 cm). The bound material was eluted at a flow rate of 1.0 cm.min$^{-1}$ with a linear gradient from 0.125 to 0.325 M sodium chloride in 0.025 M sodium phosphate at pH 7.0±0.1. Chondroitinase AC eluted in a single protein peak at 0.175 to 0.225 M sodium chloride. Purification results for the chondroitinase enzymes are shown in Table 1.

TABLE 1

Purification of chondroitinase enzymes from *Flavobacterium heparinum* fermentations

| sample | activity (IU) | specific activity (IU/mg) | yield (%) |
|---|---|---|---|
| fermentation: | | | |
| chondroitinase AC | 65,348 | 0.764 | 100 |
| chondroitinase B | 21,531 | 0.252 | 100 |
| osmolate: | | | |
| chondroitinase AC | 39,468 | 1.44 | 60 |
| chondroitinase B | 15,251 | 0.588 | 71 |
| cation exchange: | | | |
| chondroitinase AC | 27,935 | 9.58 | 43 |
| chondroitinase B | 13,801 | 4.731 | 64 |
| cellufine sulfate: | | | |
| chondroitinase AC | 18,160 | 22.6 | 28 |
| chondroitinase B | 6,274 | 21.2 | 29 |
| hydroxylapatite: | | | |
| chondroitinase AC | 14,494 | 146.8 | 22 |
| chondroitinase B | 3,960 | 65.62 | 18 |
| strong cation exchange: | | | |
| chondroitinase AC | 9,843 | 211.4 | 15 |
| chondroitinase B | 4,104 | 167.2 | 18 |
| gel filtration: | | | |
| chondroitinase B | 2,814 | 278.7 | 13 |

Chondroitinase activity was determined by a modification of the spectrophotometric assay described by Yang, et al., *J. Biol. Chem.*, 160(30):1849–1857, 1985. Chondroitinases degrade their respective substrates by an eliminative reaction resulting in the formation of 4,5-unsaturated sulfated disaccharides which absorb ultraviolet light at 232 nm. Reaction buffers contained 50 mM Tris, pH 8.0 and 0.5 mg/ml substrate; dermatan sulfate for chondroitinase B activity, chondroitin sulfate A for chondroitinase AC activity. A continuous spectrophotometric assay is carried out by transferring a 10 to 50 µl sample to a quartz cuvette and adding the reaction buffer to make a final volume of one ml. The cuvette is placed in a Beckman DU 640 spectrophotometer, controlled to maintain a constant temperature of 30° C., and the increase in absorbance at 232 nm monitored for three to five minutes. Activities are calculated using the molar extinction coefficient for chondroitin sulfate, $5.1 \times 10^3$ M$^{-1}$, and are expressed in international units, IU, where one IU is the amount of enzyme required to catalyze the formation of one µmole unsaturated product per minute.

Properties of Chondroitinase Enzymes

The purification method described herein is suitable for obtaining sufficient quantities of purified chondroitinase AC and chondroitinase B for characterization studies. The purified enzymes were analyzed by SDS-PAGE using the technique of Laemmli, *Nature*, 227:680–685, 1970, and the gels quantified with a scanning densitometer (Bio-Rad, Model GS-670). Chondroitinase AC was shown to have a molecular weight of 77,000±5,000 Daltons and a purity of greater than 99% while chondroitinase B has a molecular weight of 55,000±2,300 Daltons and a purity of greater than 99%.

Kinetic parameters of the 77,000 Dalton chondroitinase AC protein were measured using both chondroitin sulfate A and chondroitin sulfate C as substrates. The $K_m$ and $K_{cat}$ values for chondroitinase A activity were 6 µM and 230 s$^{-1}$, respectively, while the $K_m$ and $K_{cat}$ values for chondroitinase C activity were 9.3 µM and 150 s$^{-1}$, respectively. Kinetic parameters of the 55,000 Dalton chondroitinase B protein were measured using dermatan sulfate as the substrate. The $K_m$ and $K_{cat}$ values for chondroitinase B activity were 7.4 µM and 192 s$^{-1}$, respectively.

Effect of Added Reagents

The Vm$_{max}$ of the chondroitinase enzymes can be effected by trace amounts of certain elements. A base reaction buffer of 20 mM Tris buffer, pH 8.0 and 0.5 mg/ml substrate, either chondroitin sulfate A for chondroitinase AC or dermatan sulfate for chondroitinase B, was used to determine the effect of divalent metals and salts on the activity of the chondroitinase enzymes. The results are shown in Table 2.

TABLE 2

Effects of 0.1 mM of various reagents on the activity of chondroitinase enzymes.

| reagent | chondroitinase AC relative activity (%) | chondroitinase B relative activity (%) |
|---|---|---|
| none | 100 | 100 |
| MgCl$_2$ | 91 | 91 |
| MnCl$_2$ | 83 | 33 |
| CuSO$_4$ | 92 | 91 |
| ZnCl$_2$ | 26 | 45 |
| FeSO$_4$ | 98 | 69 |
| HgCl$_2$ | 55 | 40 |
| CoCl$_2$ | 81 | 42 |
| EDTA | 97 | 1 |

Stabilization of Chondroitinases

The chondroitinase enzyme activity can be stabilized by addition of excipients or by lyophilization. Stabilizers include carbohydrates, amino acids, fatty acids, and surfactants and are known to those skilled in the art. Examples include carbohydrate such as sucrose, lactose, mannitol, and dextran, proteins such as albumin and protamine, amino acids such as arginine, glycine, and threonine, surfactants such as Tween™ and Pluronic™, salts such as calcium chloride and sodium phosphate, and lipids such as fatty acids, phospholipids, and bile salts. The stabilizers are generally added to the protein in a ratio of 1:10 to 4:1, carbohydrate to protein, amino acids to protein, protein stabilizer to protein, and salts to protein; 1:1000 to 1:20, surfactant to protein; and 1:20 to 4:1, lipids to protein. Other stabilizers include high concentrations of ammonium sulfate, sodium acetate or sodium sulfate, based on comparative studies with heparinase activity. The stabilizing agents, preferably the ammonium sulfate or other similar salt, are added to the enzyme in a ratio of 0.1 to 4.0 mg ammonium sulfate/IU enzyme.

The use of stabilizers is demonstrated as follows. The purified chondroitinase enzymes were dialyzed into 10 mM sodium phosphate, pH 7.5, to a concentration of 2 IU/ml and supplemented with either 1 mg/ml bovine serum albumin, 1.5 M sodium acetate, 0.0025 M Tris or 0.15 M Tris, and an accelerated shelf life performed at 37° C. 2 IU of purified chondroitinase enzymes also were placed into various buffers, lyophilized and an accelerated shelf life performed at 37° C. The results are shown in Table 3.

TABLE 3

Stability of chondroitinase enzymes at 37° C.

| | | 7 day retention of activity (%) | |
|---|---|---|---|
| additive | format | chondroitinase AC | chondroitinase B |
| 0.15 M Tris | liquid | 1 | 42 |
| 0.0025 M Tris | liquid | 22 | 44 |
| 1 mg/ml BSA | liquid | 1 | 26 |
| 1.5 M NaOAc | liquid | 64 | 72 |
| 0.15 M Tris | lyophilized | 26.7 | 43.7 |
| PBS | lyophilized | 8.7 | 15.9 |
| 8 mg/ml sucrose | lyophilized | 88 | 93.16 |
| 2 mg/ml glycine | lyophilized | 42.4 | 75.7 |

Cloning of Chondroitinase AC and Chondroitinase B

Amino Acid Analysis

The purified proteins were analyzed by the technique of Edman, *Ann. N. Y. Acad. Sci.* 88:602, 1950, to determine the N-terminal amino acid. However, the Edman chemistry was unable to liberate an amino acid, indicating that a post-translational modification had occurred at the N-terminal amino acid of both chondroitinase proteins. One nmol samples of chondroitinases AC and B were used for deblocking with pyroglutamate aminopeptidase. Control samples were produced by mock deblocking 1 nmol samples without adding the peptidase. All samples were placed in 10 mM ammonium carbonate buffer at pH 7.5 with 10 mM dithiothreitol. 1 mU peptidase was added to the samples and the reaction allowed to incubate at 37° C. for 8 hours. An additional 0.5 mU peptidase was added and incubation continued for 16 h. The reaction mixture was exchanged into 35% formic acid by diafiltration with 10,000 Dalton cut-off ultrafiltration membranes (Centricon, Amicon) and the sample dried under vacuum. Deblocked chondroitinase enzymes were then analyzed by Edman chemistry to determine the N-terminal sequence, using an Applied Biosystems 745A Protein Sequencer.

The N-terminal sequence of chondroitinase AC was QTG-TAEL (Sequence ID No. 2, amino acids 24 to 30) and of chondroitinase B was VVASNEL (Sequence ID No. 4, amino acids 27 to 34).

The chondroitinase enzymes were subjected to enzymatic fragmentation using the arginine specific protease clostripain (EC 3.4.22.8, Sigma). Pre-activated clostripain was added to chondroitinase AC at a 1 to 2% w/w ratio in 0.025 M sodium phosphate, 0.0002 M calcium acetate and 0.0025 M dithiothreitol at pH 7.5±0.1 and incubated for 2 to 3 hours at 37° C. The reaction mixture was applied to a Vydac $C_{18}$ reverse phase HPLC column (0.46 cm I.D.×30 cm) and the peptide fragments eluted at a linear flow rate of 1 cm-min$^{-1}$ with a linear gradient of 10 to 90% acetonitrile in 1% trifluoroacetic acid. Four of the peptide fragments obtained were subjected to amino acid sequence determination.

Clostripain was added to chondroitinase B at a 1 to 2% w/w ratio in 0.025 M sodium phosphate, 0.0002 M calcium acetate and 0.0025 M dithiothreitol at pH 7.5±0.1 and incubated for 2 to 3 hours at 37° C. The reaction mixture was applied to a Vydac™ $C_{18}$ reverse phase HPLC column and the peptide fragments eluted at a linear flow rate of 6.0 cm°min$^{-1}$ with a linear gradient of 10 to 90% acetonitrile in 1% trifluoroacetic acid. Three of the peptide fragments obtained were subjected to amino acid sequence determination.

Construction of *Flavobacterium heparinum* Gene Library

A *Flavobacterium heparinum* chromosomal DNA library was constructed in lambda phage DASHII. 0.4 μg of *F. heparinum* chromosomal DNA was partially digested with restriction enzyme, Sau3A, to produce a majority of fragments around 20 kb in size, as described in Maniatis, et al., *Molecular Cloning, A laboratory Manual*, 1982. This DNA was phenol/chloroform extracted, ethanol precipitated, ligated with DASHII arms and packaged with packaging extracts from a Lambda DASHII™/BamHI Cloning Kit (Stratagene, La Jolla, Calif.). The library was titered at approximately $10^{-5}$ pfu/ml after packaging, was amplified to $10^{-8}$ pfu/ml by the plate lysis method, and stored at −70° C. as described by Silhavy et al. in *Experiments with Gene Fusions*, Cold Spring Harbor Laboratory, 1972.

The *F. heparinum* chromosomal library was titered to about 300 pfu/plate, overlaid on a lawn of *E. coli*, and allowed to transfect the cells overnight at 37° C., forming plaques. The phage plaques were transferred to nitrocellulose paper, and the phage DNA bound to the filters, as described in Maniatis, et al., ibid.

Nucleic Acid Sequence Encoding Chondroitinase AC

Degenerate primers were designed from peptides AC-1, AC-3 and AC-4 (Sequence ID No. 2, amino acids 395 to 413; 603 to 617; 514 to 536; and 280 to 288, respectively). Amplification of the primers was carried out in a 0.1 ml reaction buffer containing 50 mM KCl, 10 mM Tris/HCl pH 9, 0.1% Triton X-100, 2.5 mM $MgCl_2$, plus the four dNTPs at 200 μM, 2.5 units Taq Polymerase (Bio/Can, Mississauga, Ont.), 0.1 mM of each primer and 10 ng of *F. heparinum* genomic DNA. The amplified primers were linearized with SalI, NotI, and XbaI in individual restriction digests, and combined, after purification, for use as template DNA. The samples were placed in an automated heating block, (DNA Thermocycler™, Barnstead/Thermolyne, Dubuque, IA) programmed for cycles with temperatures of denaturation at 94° C. for 1 min., annealing at 50° C. for 2 min., and extension at 72° C. for 2 min., with 35 repetitions of this sequence. The combination of synthetic oligonucleotide primers:

5'-TCNGGRAARTARTANCCDATNGCRTCRTG-3' (Sequence ID No. 5), corresponding to peptide AC-3; and 5'-TAYATGGAYTTYAAYGTNGARGG-3' (Sequence ID No. 6), corresponding to peptide AC-4; yielded a PCR product of approximately 750 bp in size. Attempts to clone this fragment into vectors, pTZ/PC or into pCRII (TA cloning kit, Invitrogen, San Diego, Calif.) in *E. coli* strain, FTB1, were unsuccessful.

*E. coli* FTB1 was constructed as follows: the F' episome from *E. coli* XL-1 Blue, (Stratagene, La Jolla, Calif.) carrying the lac $I^q$ repressor gene was moved, as described by Miller, *Experiments in Molecular Genetics*, Cold Spring Harbor, 1972, into *E. coli* TB1 described by Baker et al., *Proc. Natl. Acad. Sci.* 81:6779–6783, 1984. The FTB1 background permits a more stringent repression of transcription from plasmids carrying promoters with a lac operator such as the lac and tac promoters.

To facilitate cloning of these PCR products, a restriction site was incorporated at the 5' ends of the primers. The PCR products were analyzed for the absence of restriction sites which are found in the multiple cloning site of pBluescript (Stratagene, La Jolla, Calif.) to determine which restriction site should be added to the primers. This ensured that the PCR products would not be cut into multiple fragments when treated with the restriction enzyme used to form overhangs on the ends of the DNA fragments. BamHI met this criteria for all three PCR fragments. New primers were synthesized with BamHI sites at their 5' ends, which were otherwise identical to those described above, and used to produce a 764 bp PCR product, FIG. 1. This DNA fragment was digested with BamHI, isolated on an agarose gel, as described by Maniatis et al., ibid, and purified using the Geneclean™ kit (Bio/Can, Mississauga, Ont.) pBluescript was digested with BamHI, the 5' ends dephosphorylated by alkaline phosphatase treatment as described by Maniatis et al., ibid, and purified from an agarose gel using the Geneclean™ kit. The treated PCR fragment and pBluescript plasmid DNA were ligated, transformed into FTB1, and plated onto LB agar plates containing ampicillin at 0.2 mg/ml. Plasmids from colonies grown on these plates were isolated by colony cracking as described in Maniatis et al., ibid. All enzymes were supplied by New England Biolabs (Mississauga, Ont.). Plasmids were isolated using the RPM™ kit (Bio/Can, Mississuaga, Ont.). Sequence analysis of the cloned PCR fragment correlated with reverse transcribed peptide sequences from chondroitinase AC peptides, indicating that the PCR fragment encodes the chondroitinase AC gene. DNA sequencing was performed by the dideoxy-chain termination method of Sanger et al., *Proc. Natl. Acad. Sci.*, 74:5463–5467, 1978. Sequencing reactions were carried out with the Sequenase™ Kit (U.S. Biochemical Corp., Cleveland, Ohio) and S-dATP (Amersham Canada Ltd., Oakville, Ontario, Canada), as specified by the supplier.

The 764 bp PCR fragment, contained in plasmid pA2C1BS-11 represents approximately 36% of the coding region for the Chondroitinase AC gene. This entire 764 bp fragment was sequenced and was found to contain a continuous open reading frame which encoded peptides AC-3, AC-4 and AC-1 (Sequence ID No. 2, amino acids 395–413; 603–617; 514–536; 280–288, respectively).

The 764 bp PCR fragment was used to probe the genomic *F. heparinase* lambda library. First, pA2C1BS-11 was isolated via the boiling method, as described in Maniatis et al., ibid. The plasmid was digested with BamHI, separated from the vector, purified as described above and labeled with a Nick Translation™ kit (Boehringer Mannheim, Montreal, Canada) using radiolabelled $^{32}$p α-dATP. *E. coli* P2392 (Stratagene, La Jolla, Calif.) was used as the lawn for plating the lambda library. Approximately 6000 plaques were screened by plaque hybridization using BA85 nitrocellulose membranes (Scheicher & Schuell, Keene, NH) as described by Maniatis et al., ibid. Plaque hybridization was carried out, at 65° C. for 16 hours in a Tek Star™ hybridization oven (Bio/CAN Scientific, Mississauga, Ontario). Subsequent washes were performed at 65° C., twice for 15 min. in 2×SSC, once in 2×SSC/0.1% SDS for 30 min. and once in 0.5×SSC/0.1% SDS for 15 min. More than 100 positive plaques were identified and isolated, some of which were clusters of plaques. These were rescreened by spotting the lambda clone onto a lawn of P2392 host cells and reprobing via plaque hybridization. Six plaques were positive upon rescreening, and their DNA was isolated, as described by Maniatis, et al., ibid, and digested with restriction enzymes corresponding to the sites on the ends of lambda DASH II arms. This DNA was used in Southern hybridization analysis (Southern, *J. Mol. Biol.* 98:503–517, 1975) by blotting onto Hybond™ N nylon membrane (Amersham, Oakville, Canada) using hybridization and wash conditions, described above for plaque hybridization. One clone contained a 4.5 kb Sal I fragment and another contained a 6 kb BamHI fragment, both of which hybridized with the probe. These were cloned into corresponding sites of pBluescript.

Because the molecular weight of chondroitinase AC is approximately 75 kD, the size of the corresponding gene would be approximately 2.05 kb. Both the 4.5 kb SalI and the 6 kb BamHI chromosomal DNA fragments could include the entire chondroitinase AC gene. To increase the probability of analyzing a DNA fragment which encodes the entire gene, the 6 kb BamHI fragment was chosen for sequence analysis. The pBluescript plasmid containing this BamHI fragment (called p64BS2-7, FIG. 1) was isolated using the Qiagene kit (Bio/Can, Miss, Ont). A method of DNA sequencing, the walking primer strategy (Voss et al. *Meth. Molec. Cell. Biol.* 3:153–155 (1992)), was employed using synthetic primers (Eppendorf, model ECOSYN™ D300, Madison, Wis.) and an A.L.F. DNA sequencer (Pharmacia LKB, Mtl, Qc). Fluorescenated Universal and Reverse primers provided in the Pharmacia AutoRead kit were also used. Fluorescently labeled dNTPs were incorporated into sequencing reactions with the Pharmacia AutoRead Fluorescent labelling kit (Pharmacia LKB, Mtl, QC). Areas of secondary structure were resolved by one of two methods. First, fluorescenated primers which hybridized close to, and 5' to, the region of secondary structure were synthesized. Using these primers, the Pharmacia AutoCycle™ kit (Pharmacia LKB, Mtl, Qc), and a automated heating block (DNA Thermocycler™, Barnstead/Thermolyne, Dubuque, Iowa), programmed for step cycles of 95° C. for 36 sec, 500° C. for 36 sec and 72° C. for 84 sec, repeated 25 times, sequencing of secondary structure regions was accomplished. Any ambiguous areas still not resolved by the first method were sequenced by the method of Sanger et al., *Proc. Natl. Acad. Sci.* 74: 5463–5467 (1978), using $^{35}$S a-dATP, and a USB Sequenase™ kit (LaJolla, Calif.) in which dGTP was replaced by dITP.

Analysis of the DNA sequence indicated that there was a single, continuous open reading frame of 2100 bp containing codons for 700 amino acid residues. All four clostropain-derived peptides were encoded by this gene. Searching for a possible signal peptide sequence using Geneworks™ (Intelligenetics, Mountain View, Calif.), suggested that there are two possible sites for the processing of the protein into a mature form: Q-23 (glutamine) and A-28 (alanine). N-terminal amino acid sequencing of deblocked, processed Chondroitinase AC indicated that the mature protein begins with Q-23 and contains 678 amino acids with a calculated molecular weight of 77,169 Daltons.

Expression of Chondroitinase AC in *E. coli*

Figure 2:
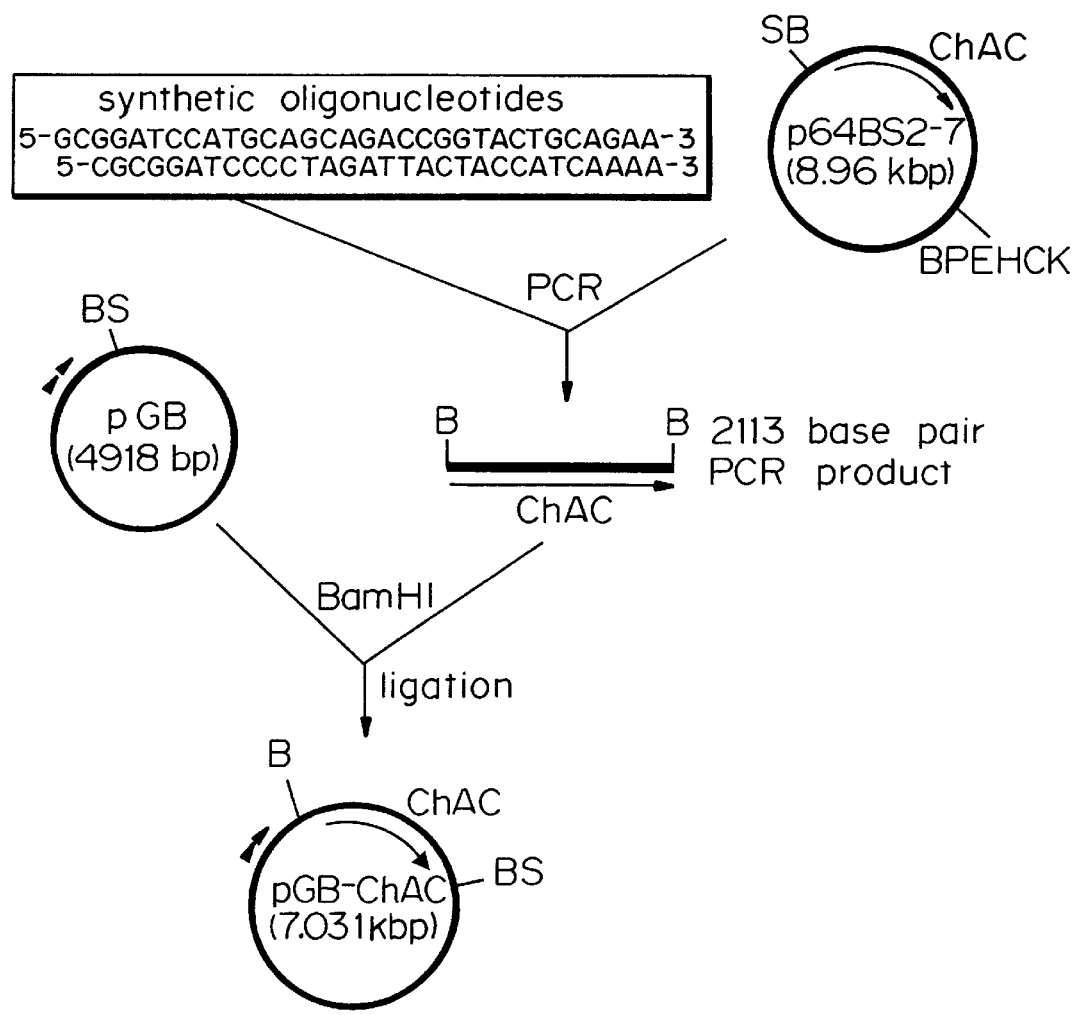
FIG. 2 is a schematic of the construction of pGB-ChAC, a plasmid capable of directing the expression of active chondroitinase AC in *E. coli* from tandem tac promoters (double arrowheads).

Construction of an expression vector for chondroitinase AC is shown in FIG. 2. The vector pGB is an *E. coli* expression vector which contains an unique BamHI site, whereby expression of a DNA fragment inserted into this site is driven by a double tac promoter. The vector also includes a kanamycin resistance gene and the lac I$^q$ gene to allow induction of transcription with IPTG. PCR was used to generate a mature chondroitinase AC gene.

An oligonucleotide, 5'-GCGGATCCATGCAGCAGA CCGGTACTGCAGAA-3', (Sequence ID No. 7) was designed to insert an ATG-start site immediately preceding the codon for the first amino acid (Q-23) of mature chondroitinase AC, while an oligonucleotide 5'-CGCGGATCCCCTAGATTACTACCATCAAAA-3' (Sequence ID No. 8) was designed to hybridize downstream of the TAG-stop codon. Both oligonucleotides also contain a BamHI site. Plasmid p64BS2-7 was used as the template in a PCR reaction with an annealing temperature of 45° C. A specific fragment of the expected size of 2034 bp was obtained. This fragment was isolated and inserted into a BamHI site of the expression vector pGB.

The construct was transformed into *E. coli* strain, F-TB1, and the transformed bacteria was grown at 37° C. in LB medium containing 75 µg/ml kanamycin to an $OD_{600}$ of 0.5, at which point the tac promoter from pGB was induced by the addition of 1 mM IPTG. Cultures were grown an additional 2 to 5.5 hours at either 23° C., 30° C. or 37° C. The cells were cooled on ice, concentrated by centrifugation and resuspended in cold PBS at 1/10th the original culture volume. Cells were lysed by sonication and cell debris removed by centrifugation at 10,000×g, 5 minutes. The pellet and supernatant fractions were analyzed separately for chondroitin sulfate A or C degrading (chondroitinase AC) activity. Chondroitin sulfate A degrading activities of $1.24 \times 10^{-2}$, $2.88 \times 10^{-2}$, and $4.25 \times 10^{-2}$ IU/ml/OD and chondroitin sulfate C degrading activities of $1.57 \times 10^{-2}$, $2.24 \times 10^{-2}$, and $6.02 \times 10^{-2}$ IU/ml/OD were observed from cultures grown at 23, 30 and 37° C., respectively. The activities using chondroitin sulfate A as the substrate are approximately twice that of those using chondroitin sulfate C as the substrate. This ratio is also observed when measuring the activity of the wild type chondroitinase AC using both these substrates.

E. coli F-TB1(pGB-ChAC) was grown in a 3.5 L Braun Biostat E computer controlled fermenter in M9 medium to a dry cell weight concentration of 35 g/L. Glucose and ammonia were added as needed to maintain growth and pH at 7.0. Chondroitinase A activity accumulated to 103.44 IU/ml while chondroitinase C activity accumulated to 28.26 IU/ml.

Nucleic Acid Encoding Chondroitinase B

Partial-guessmer PCR primers were designed using the amino acid sequences of the clostripain-generated peptides from the chondroitinase B protein and the codons commonly found in Flavobacterium genes, Table 4. Three peptides were generated, designated CHB-1 (Sequence ID No. 4, amino acids 373 to 384), CHB-2 (Sequence ID No. 4, amino acids 41 to 50), and CHB-3 (Sequence ID No. 4, amino acids 130 to 146).

TABLE 4

Codon usage table for Flavobacterium and Escherichia coli.

| amino acid codon(s) | | consensus codon | |
|---|---|---|---|
| | | E. coli | Flavobacterium |
| A | GCT, GCC, GCG, GCA | GCT | GCC |
| C | TGT, TGC | EITHER | EITHER |
| D | GAT, GAC | EITHER | EITHER |
| E | GAG, GAA | GAA | GAA |
| F | TTC, TTT | EITHER | TTT |
| G | GGC, GGA, GGG, GGT | GGC or GGT | GGC |
| H | CAC, CAT | CAT | CAT |
| I | ATC, ATA, ATT | ATA | ATC |
| K | AAA, AAG | AAA | AAA |
| L | CTT, CTA, CTG, TTG, TTA, CTC | CTG | CTG |
| M | ATG | ATG | ATG |
| N | AAC, AAT | AAC | AAT |
| P | CCC, CCT, CCA, CCG | CCG | CCG |
| Q | CAG, CAA | CAG | CAG |
| R | CGT, AGA, CGC, CGA, AGG, CGG | CGT | CGC |
| S | TCA, TCC, TCG, TCT, AGC, AGT | TCT | ND |
| T | ACG, ACC, ACT, ACA | ACC or ACT | ACC or ACA |
| V | GTC, GTA, GTT, GTG | GTT | ND |
| W | TGG | TGG | TGG |
| Y | TAC, TAT | EITHER | TAT |

5'-CGG GAT CCC ARA TYG CCG AYG GNA CNT ATA AAG A-3' (Sequence ID No. 9) was derived from the CHB-2 peptide (Sequence ID No. 4, amino acids 41 to 50) and 5'-CGG GAT CCG GCN SKA TTG CGT TCR TCA AA-3' (Sequence ID No. 10) was derived from peptide CHB-3, Sequence ID No. 4, amino acids 130 to 146. A BamHI site was present on the 5' end of each primer to increase the efficiency of cloning of the PCR product. Using linear F. heparinum chromosomal DNA, described above, as a template, a single 300 bp DNA fragment was amplified. Conditions for the amplification were as follows: denaturation at 94° C. for 40 sec, annealing at 45 or 50° C. for 1 min. and extension at 72° C. for 2 min. This cycle was repeated 35 times.

Figure 3:
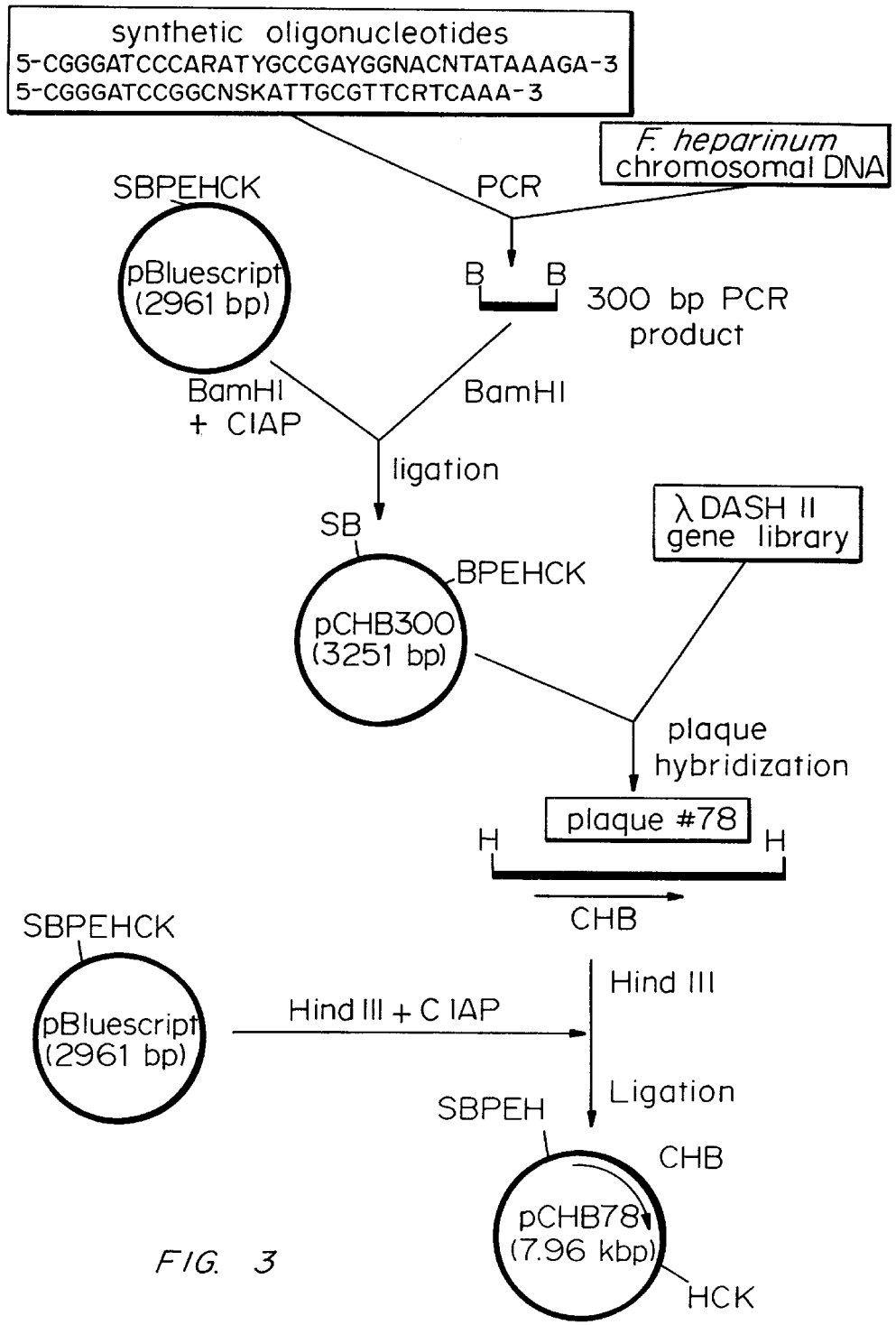
FIG. 3 is a schematic of the construction of plasmids used to sequence the chondroitinase B gene from *Flavobacterium heparinum*, pCHB300 and pCHB78.

As shown in FIG. 3, the PCR fragment was purified on an agarose gel, digested with BamHI and ligated into BamHI digested, dephosphorylated pBluescript. The ligation mixture was used to transform E. coli FTB1. Of the 50 resulting transformants, one yielded a 300 bp fragment when cut with BamHI. The insert in this plasmid, pCHB300, was subjected to DNA sequence analysis, performed as described above, which revealed that the insert contained DNA sequences outside of the primer regions which encoded amino acid sequence matching that determined for two chondroitinase B peptides. This insert was used to screen the lambda library of F. heparinum chromosomal DNA, which was constructed as described above.

The lambda library was plated with a density of 200 plaques per dish. Plate lifts of 20 dishes were made. For production of the probe, 500 ng of pCHB300 was submitted to 30 cycles of PCR amplification; denaturation at 93° C., annealing at 55° C. and extension at 72° C., each for 1 min., using the primers described above. The resulting PCR fragment was purified on agarose gels and labelled with $dATPa^{32}P$, using the Random Primer labelling kit (Boehringer Mannheim, Laval, Canada). Thirty-one potential lambda clones were found which hybridized with this probe, after the lifts were subjected to washing one time, in 2× SSC at 58° C. Rescreening of these plaques gave a positive signal for 17 of the plaques after washing at 58° C., 2× for 15 min. in 2× SSC, 1× for 30 min. in 2× SSC/0.1% SDS and 1× for 20 min. in 0.5× SSC/0.1% SDS. Two of 8 clones analyzed further showed a 5.0 kb HindIII fragment hybridizing with the probe and comigrating with a HindIII fragment from F. heparinum chromosomal DNA which also hybridized with the 300 bp probe. The 5.0 kb fragment was gel purified from both lambda clones, ligated into the HindIII site of pBluescript and transformed into FTB1.

44 colonies were picked and rubbed on the side of a 0.5 ml PCR tube containing 20 gl of the same PCR mixture as above. PCR was performed at: denaturation at 930° C., for 30 sec., annealing at 580° C., for 30 sec. and extension at 72° C., for 1 min, for 35 cycles. Upon analysis, 6 transformants showed amplification of the 300 bp band. DNA from these colonies were isolated and digested by HindIII revealing the presence of a 5.0 kb fragment. 5 out of the 6 clones hybridized with the 300 bp fragment, confirming results of the PCR amplification experiment. One of these clones, pCHB78, was selected and used as a template for DNA sequencing.

Using a walking primer strategy, sequencing reactions were carried out as described above for the A.L.F. DNA sequencer. Sequence analysis revealed a single 1.52 kb open reading frame coding for 506 amino acid residues. The preprotein was found to have a signal peptide of 25 amino acids. The mature chondroitinase B enzyme contains 481 amino acids with a calculated molecular weight of 53,563 daltons.

Expression of Chondroitinase B in E. coli

Figure 4:
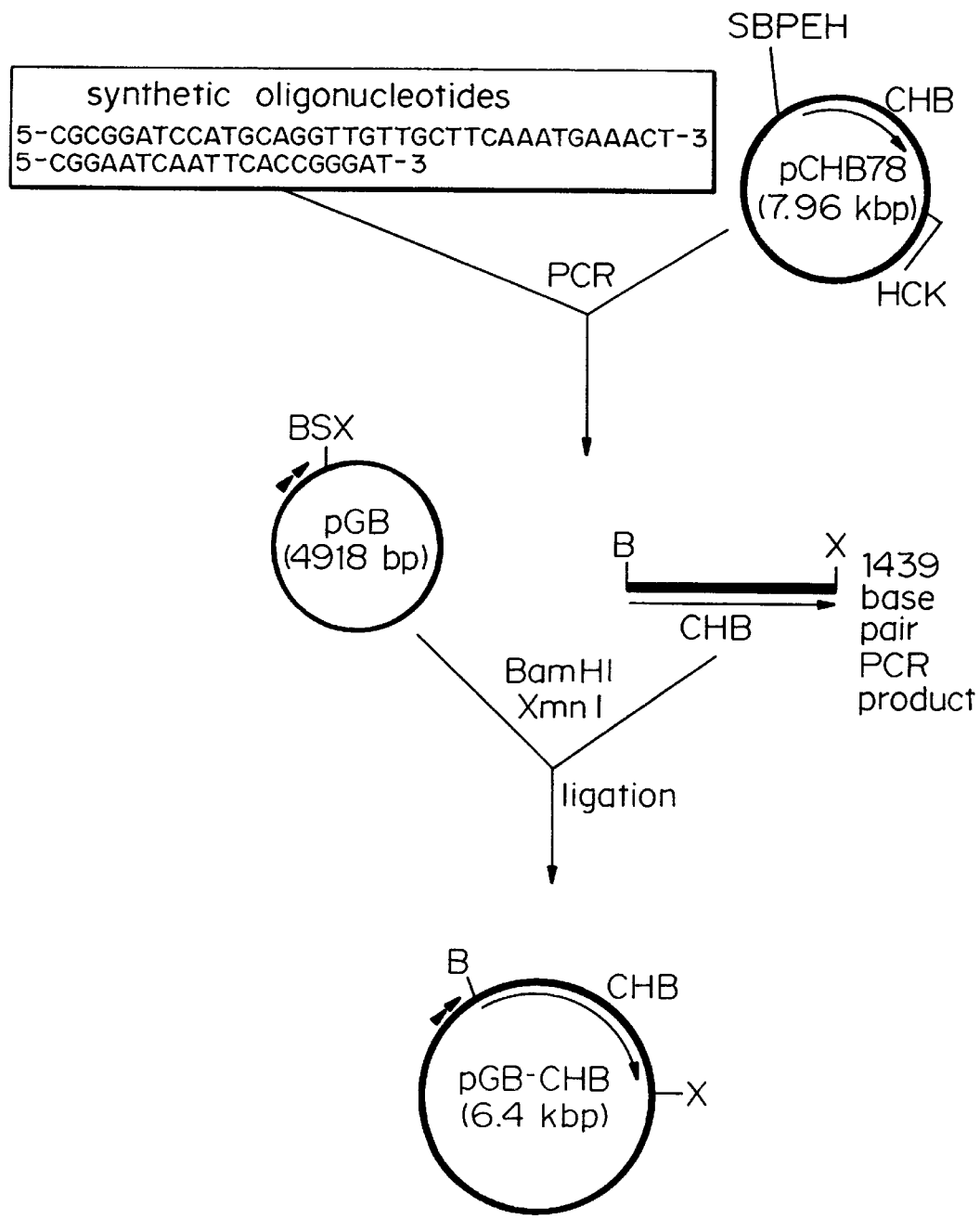
FIG. 4 is a schematic of the construction of pGB-CHB, a plasmid capable of directing the expression of active chondroitinase B in *E. coli* from tandem tac promoters (double arrowheads).

Construction of an expression vector for chondroitinase B is shown in FIG. 4. Primers were designed to amplify the coding region of the chondroitinase B gene in an analogous manner to that described above with reference to expression of the chondroitinase AC gene. One oligonucleotide used for amplification of the chondroitinase B coding sequence (5'-CGCGGATCCATGCAGGTGTTGCTCAAATGAAACT-3') (Sequence ID No. 11), contained a BamHI restriction site at its 5' end and an ATG codon that was to be inserted before the first amino acid of the mature protein. The second oligonucleotide (5'-CGGAATCAATTCACCGGG-AT-3') (Sequence ID No. 12) was designed with a XmnI restriction site and a termination codon to be inserted at the end of the coding sequence of the gene. Using 100 ng of pCHB78 as template, with an annealing temperature of 520° C., the 1.5 kb fragment was amplified, gel purified, restriction digested and inserted into pGB previously cut with BamHI and XmnI. This resulted in the definitive pGB-CHB construct used to express the protein.

This construct was transformed in *E. coli* strain DH5α, expressed as described for the chondroitinase AC enzyme. After growing cells until an O.D. 600=0.5, 1 mM IPTG was added to the cultures to induce the tandem tac promoters and cells were transferred to either 23° C., 300° C. or 37° C. for additional growth for 5, 3 and 2 hours, respectively. After sonication, supernatant fractions were assayed for activity on dermatan sulfate. Growth of cells at 230° C. gave the best results with a degrading activity of 0.57 IU/ml/OD while growth of cells at 30° C. and 37° C. gave degrading activities of 0.14 and 0.01 IU/ml/OD respectively.

The present invention describes a methodology for obtaining highly purified chondroitin degrading enzymes derived from the natural organism *Flavobacterium heparinum*, and the genes encoding these enzymes. Derivatives of the genes can be prepared by making conservative substitutions, additions and deletions thereof, which do not substantially impact on the resulting enzymatic activity, or by using degenerative forms of the genes. As used herein, conservative substitutions involve substitutions of codons which encode the same amino acids and substitutions of amino acids for amino acids having similar structure or chemical characteristics, which are well known to those skilled in the art, for example, groups of structurally similar amino acids include (I,L,V); (F,Y); (K,R); (Q,N); (D,E); AND (G,A).

Variations of these methods will be obvious to those skilled in the art from the foregoing detailed description of the invention. Such modifications are intended to come within the scope of the appended claims.

---

We claim:

1. An isolated nucleic acid fragment having the sequence of Sequence ID No. 1 or naturally occurring sequences having conservative or degenerative substitutions thereof, encoding chondroitinase AC.

2. The nucleic acid fragment of claim 1 encoding chondroitinase AC having the amino acid sequence of Sequence ID No. 2.

3. The nucleic acid fragment of claim 1 having the sequence of Sequence ID No. 1.

4. An isolated nucleic acid fragment having the sequence of Sequence ID No. 3 or naturally occurring sequences having conservative or degenerative substitutions thereof, encoding chondroitinase B.

5. The nucleic acid fragment of claim 4 encoding chondroitinase B having the amino acid sequence of Sequence ID No. 4.

6. The nucleic acid fragment of claim 4 having the sequence of Sequence ID. No. 3.

* * * * *